United States Patent [19]

Pluskal et al.

[11] Patent Number: 5,004,543

[45] Date of Patent: Apr. 2, 1991

[54] CHARGE-MODIFIED HYDROPHOBIC MEMBRANE MATERIALS AND METHOD FOR MAKING THE SAME

[75] Inventors: Malcolm G. Pluskal, Bedford; David Wang, Lexington; Michael J. Steuck, North Reading, all of Mass.

[73] Assignee: Millipore Corporation, Bedford, Mass.

[21] Appl. No.: 209,307

[22] Filed: Jun. 21, 1988

[51] Int. Cl.$^5$ ............................................. B01L 67/00
[52] U.S. Cl. .............................. 210/490; 210/500.36; 210/500.37; 427/245
[58] Field of Search .................. 210/500.39, 638, 490, 210/500.23, 500.36, 500.29; 427/244, 245, 246, 307

[56] References Cited

U.S. PATENT DOCUMENTS

| | | | |
|---|---|---|---|
| 2,926,116 | 2/1960 | Keim | 162/164 |
| 2,926,154 | 2/1960 | Keim | 260/29.2 |
| 3,083,118 | 3/1963 | Bridgeford | 427/307 X |
| 3,224,986 | 12/1965 | Butler et al. | 260/29.2 |
| 3,311,594 | 3/1967 | Earle, Jr. | 260/77.5 |
| 3,332,901 | 7/1967 | Keim | 260/29.2 |
| 3,382,096 | 5/1968 | Boardman | 117/139.5 |
| 3,723,306 | 3/1973 | Bridgeford | 210/500.29 X |
| 3,761,350 | 9/1973 | Munjat et al. | 162/164 |
| 3,876,738 | 4/1975 | Marinaccio et al. | 264/41 |
| 4,012,324 | 3/1977 | Gregor | 210/503.37 |
| 4,014,798 | 3/1977 | Rembaum | 210/500.37 X |
| 4,203,847 | 5/1980 | Grandine | 210/490 |
| 4,203,848 | 5/1980 | Grandine | 264/38 |
| 4,473,474 | 9/1984 | Ostreicher et al. | 210/636 |
| 4,512,896 | 4/1985 | Gershoni | 210/635 |
| 4,601,828 | 7/1986 | Gershoni | 210/635 |
| 4,618,533 | 10/1986 | Steuck | 428/315.7 |
| 4,673,504 | 6/1987 | Ostreicher et al. | 210/500.22 |
| 4,702,840 | 10/1987 | Degen et al. | 521/27 X |
| 4,778,596 | 10/1988 | Linder et al. | 210/638 |

FOREIGN PATENT DOCUMENTS 0005536 11/1979 European Pat. Off. .

OTHER PUBLICATIONS

Messing, *Methods in Enzymology*, 101:20 (1983).
Maniatis, *Molecular Cloning*, 387 (1982).
Matsudaira, *J. Biol. Chem.*, 262(21):10035 (1987).
Gershoni, "Protein Blotting and the Characterization of Protein Complexes", *Analytivcal Electrophoresis*, 305-313.
Gershoni, *TIBS*, 103 (Mar. 1985).
Gershoni et al., *Anal. Biochem.*, 131:1 (1983).

*Primary Examiner*—Frank Spear
*Attorney, Agent, or Firm*—Hamilton, Brook, Smith & Reynolds

[57] ABSTRACT

A hydrophobic material having a crosslinked, cationic charge-modifying coating such that the majority of the ion exchange capacity of the material is provided by fixed formal positive charge groups is disclosed. The material is produced by contacting a hydrophobic substrate with a mildly alkaline, aqueous organic solvent solution into which has been dissolved a cationic charge-modifying agent. The charge-modifying agent comprises a water soluble, organic polymer having a molecular weight of greater than about 1000, wherein the polymer chain contains both fixed formal positive charge groups and halohydrin groups.

Materials of the type described herein can be used in a variety of applications including macromolecular blotting and filtration.

18 Claims, 3 Drawing Sheets

Dot-Blot Hybridization Analysis using Charge Modified Microporous Membranes: Use of a range of concentration of DNA adsorbed to the test membrane samples.

Dot-Blot Hybridization Analysis using Charge Modified Microporous Membranes: Use of a range of concentration of DNA adsorbed to the test membrane samples.

NYLON          CHARGE MODIFIFIED PVDF.

DNA Loading

Southern Blotting Analysis using Charge Modified Microporous Membranes.

DNA Loading;

Lane #1  1.0ug
  ..   2  0.1ug
  ..   3  0.05ug
  ..   4  0.005ug

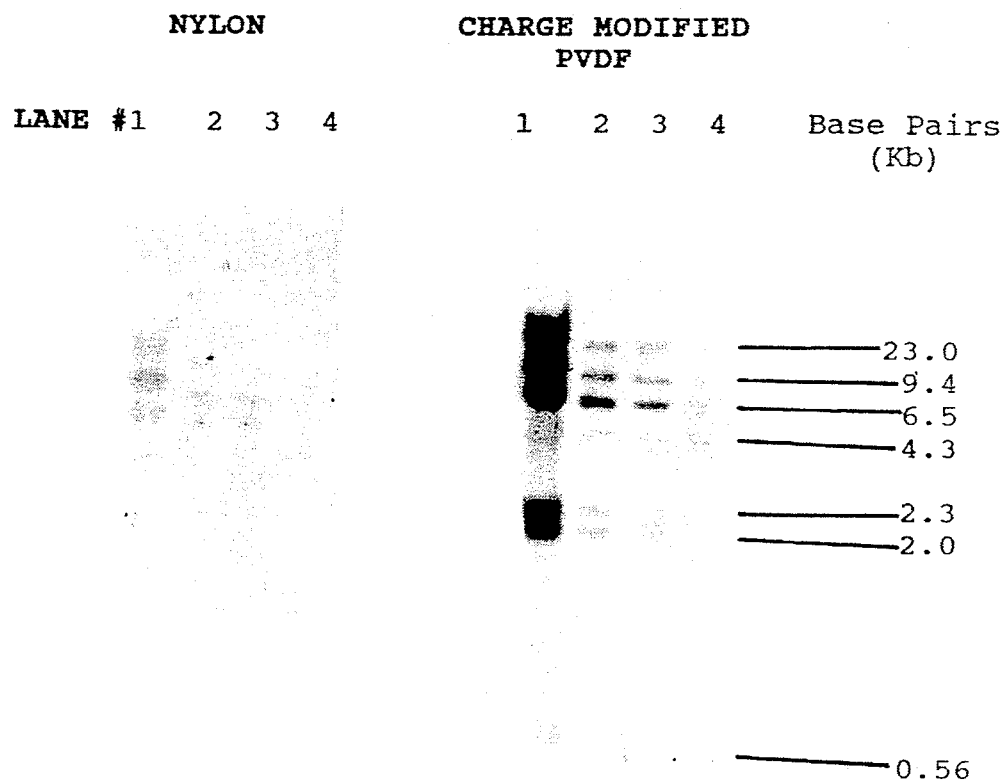

CHARGE-MODIFIED HYDROPHOBIC MEMBRANE MATERIALS AND METHOD FOR MAKING THE SAME

BACKGROUND OF THE INVENTION

Microporous membranes have been demonstrated to have utility in a wide variety of applications. As such, numerous processes have been developed to produce such membranes. For example, U.S. Pat. No. 3,876,738 described a process for preparing a microporous membrane by quenching a solution of a film forming polymer in a non-solvent system for the polymer. European Patent Application No. 0 005 536 describes a similar process.

Commercially available microporous membranes, comprising for example nylon, are available from Pall Corporation, Glen Cove, N.Y. under the trademark ULTIPOR $N_{66}$. Additionally, microporous membranes made of cellulose acetate, cellulose nitrate or mixtures thereof are widely available from a variety of sources. Other membranes, comprising yvinylidene fluoride, (PVDF), are available under the trademark Durapore ® (Millipore Corporation, Bedford, Mass.). The nylon and nitrocellulose membranes exhibit hydrophilic properties, while the PVDF membranes are hydrophobic. It is possible, however, to coat the PVDF membranes with materials which render them hydrophilic. These hydrophilic Durapore ® membranes are also available from the Millipore Corporation.

For certain applications, notably filtration and macromolecular transfer, it has been suggested that the performance of the material could be increased by providing an ionic functional group attached to the membrane surface which would serve to provide a fixed formal positive charge to the membrane. Such charge-modified membranes have been suggested for macromolecular transfer applications (e.g., DNA and blotting) in U.S. Pat. Nos. 4,512,896 and 4,601,828. Additionally, charge-modified membranes have been suggested for use as filtration materials in U.S. Pat. Nos. 4,473,474 and 4,673,504. In each of these, however, the invention is limited to methods for charge-modifying hydrophilic membranes and the use of the same. In fact, the latter two patents each provide an example describing unsuccessful attempts to charge-modify hydrophobic membranes. These attempts led to the conclusion in each of the patents that hydrophobic polymer membranes were not amenable to charge-modification by the methods attempted and described.

As such, the charge-modified microporous membranes used for macromolecular blotting and filtration applications have utilized hydrophilic membranes as starting materials.

The term "macromolecular blotting" as used herein refers to processes for transferring biological macromolecules such as nucleic acids and proteins from electrophoresis gels to some type of immobilizing matrix. Historically, nitrocellulose was used as a suitable blotting matrix. Of particular importance is nucleic acid blotting such as DNA blotting. A variety of DNA blotting techniques have been developed. The most common is referred to as "Southern Blotting". In this technique, DNA fragments are separated by chromatographic techniques and then denatured while still in the gel. The gel is neutralized and placed between wicking paper which is in contact with a buffer reservoir. Nitrocellulose is then placed on top of the gel and dry blotting papers are placed on top of the nitrocellulose. As the buffer flows into the gel, DNA is eluted and binds to the nitrocellulose, thereby transferring the DNA fragment pattern onto the nitrocellulose. The fragment pattern can then be detected using hybridization techniques employing labelled nucleic acids which are complementary to the specific bound fragments.

Since the development of the Southern blotting technique, a number of variations and improvements on the technique have been developed. For example, if the blotting paper is derivatized with diazobenzyloxymethyl groups, thereby forming a material commonly referred to as DBM-paper, RNA and proteins can be covalently attached to the material. Aminophenylthioether coated papers activated to the diazo form, (DPT-paper), can also be used to bind DNA, RNA and proteins. Other immobilization methods have used high salt or alkaline conditions in efforts to improve binding of DNA, RNA and proteins.

Other attempts to improve the binding process have concentrated on the blotting substrate by replacing nitrocellulose, for example, with other hydrophilic materials such as Nylon 66. Additionally, U.S. Pat. Nos. 4,512,896 and 4,673,504, previously described, suggest other materials such as hydrophilic PVDF for use as blotting substrates. These substrates, however, are again limited to producing hydrophilic materials which have been charge-modified. While these materials are an improvement over nitrocellulose, DBM-paper and DPT-paper, their charge retention, during hybridization and recycling, and performance under alkaline conditions could still be improved upon.

SUMMARY OF THE INVENTION

This invention pertains to charge-modified, hydrophobic substrates and methods for making and using the same. More specifically, this invention pertains to charge-modified, hydrophobic, microporous membranes characterized by having the majority of the ion exchange capacity of the material provided by fixed formal positive charge groups. These materials exhibit a combination of ionic and hydrophobic properties rendering them highly effective for macromolecular adsorption applications under a variety of conditions.

The fixed formal positive charge results, in one embodiment, largely from quaternary ammonium functional groups which can be provided on the hydrophobic surface by contacting the hydrophobic material with a solution containing a polyamine or polyamidopolyamine epichlorohydrin cationic resin to provide a surface coating. There is no need to provide a secondary charge-modifying agent to stabilize the coating or enhance the cationic charge on the microporous surface.

The materials of the instant invention are particularly well suited for applications such as macromolecular blotting and filtration. In the case of macromolecular blotting, the combination of hydrophobic and ionic effects provides a material them during hybridization, and maintain signal strength throughout a number of repeated recycling stages.

BRIEF DESCRIPTION OF THE DRAWINGS

FIG. 3 is an autoradiogram similar to that of FIG. 2 in which a second $^{32}P$ labelled DNA probe has been utilized.

DETAILED DESCRIPTION OF THE INVENTION

Figure 1:
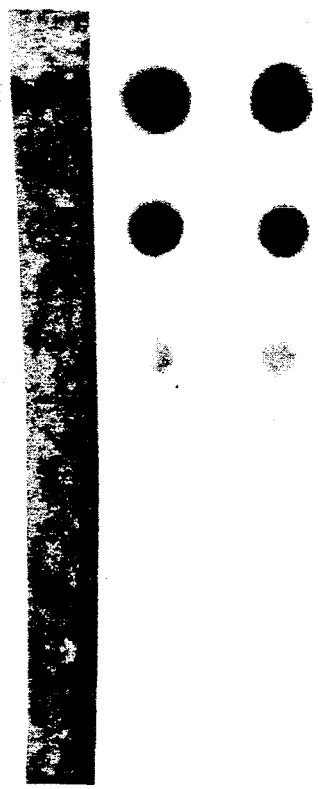
FIG. 1 is an autoradiogram comparing a nylon membrane to a charge modified microporous membrane for a dot-blot hybridization analysis.

The cationic charge-modified substrates of this invention comprise hydrophobic, microporous membranes which have been charge-modified with fixed formal charge groups having a net positive charge. The performance of these charge-modified membranes results from a combination of the hydrophobic and ionic surface effects.

The term "microporous membrane" as used herein defines a substantially isotropic porous membrane having an average pore size of at least 0.05 microns or an initial bubble point (IBP) in water of less than 120 psi. A maximum pore size useful for the invention is about 10 microns. The term "isotropic" or "symmetrical" as used herein means that the pore structure is substantially uniform throughout the membrane. In addition, "anisotropic" or "asymmetrical" membranes are also available formed as a composite between a thin layer of a material having a small average pore size supported by a more porous structure.

While membranes useful for this invention include those comprising hydrophobic polypropylene, polyethylene, polysulfone and polytetrafluoroethylene (PTFE), membranes comprising polyvinylidene fluoride (PVDF) are preferred. PVDF membranes are known in the art, being described, for example, in U.S. Pat. Nos. 4,203,848 and 4,203,847, both of Grandine, 2nd, the teachings of which are incorporated herein by reference. Furthermore, these hydrophobic membranes are commercially available as, for example, Immobilon P ® microporous membranes (Trademark of Millipore Corporation, Bedford, Mass.).

The charge-modifying agent used in this invention is a water soluble organic polymer having a molecular weight greater than about 1000, wherein the polymer comprises monomers, the majority of which have been reacted with epichlorohydrin. The epichlorohydrin serves to convert tertiary amine structures previously resident on the polymer to structures having a quaternary functionality. This . provides a stable coating which comprises a quaternary ammonium fixed formal charge capable of conferring a net positive charge to the hydrophobic substrate.

The charge-modifying agent is coated onto the contacted surfaces of the hydrophobic microporous membrane. The term "coated" as used herein refers to charge-modifying agents which are sufficiently attached to the membrane so that they will not significantly extract under the intended conditions of use.

The charge-modifying resins are preferably polyamine epichlorohydrin cationic resins, such as those described in U.S. Pat. Nos. 2,926,116; 2,926,154; 3,224,986; 3,311,594; 3,332,901; 3,382,096; and 3,761,350, of which the teachings of each are incorporated herein by reference.

It is required that the charge-modifying agent contain halohydrin substituents as well as fixed formal positive charge groups. Agents containing epichlorohydrin substitutents and quaternary ammonium ions are most preferred. One such charge-modifying agent is the polyamine epichlorohydrin resin available commercially as R4308 resin (Trademark of Hercules Corp., Wilmington, Del.). In this resin, the charged nitrogen atom forms part of a heterocyclic grouping, and is bonded through a methylene moiety to a pendent chlorohydrin group. Each monomer group of Hercules R4308 is represented by the following general formula:

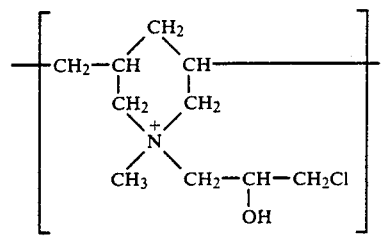

Another preferred charge modifying agent is Polycup 1884 (Trademark of Hercules Corp., Willington, Del.), the individual monomers of which are represented by the following general formula:

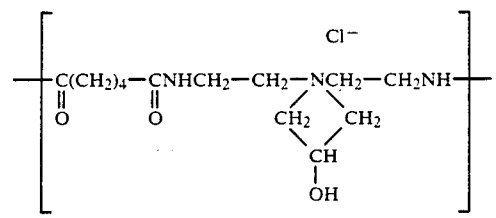

It must be pointed out, however, that ions other than ammonium ions, such as sulfonium, phosphonium or the like which form fixed formal positive charge groups can be used in the practice of this invention as well.

In the broadest sense, the process of this invention is directed to cationically charge-modifying a hydrophobic organic polymeric material, such as for example, a microporous membrane in a manner such that the majority of the ion exchange capacity of the material is provided by fixed formal positive charge groups. The process comprises applying to the membrane a charge-modifying amount of the cationic charge-modifying agent which coats the membrane structure and is cross-linked through the halohydrin substituent and residual tertiary amines in the resin. In its broadest embodiment, the process comprises the steps of:

(a) providing a hydrophobic material substrate;

(b) contacting the substrate with a charge-modifying solution, said solution comprising a charge modifying agent which comprises an organic polymer having a molecular weight of greater than about 1000, the polymer having a polymer chain having fixed formal positive charge groups as a result of halohydrin substitution; said charge-modifying agent being dissolved in an alkaline, water-miscible, organic solvent solution; and (c) curing the cationic charge-modified, hydrophobic substrate.

As stated previously, the hydrophobic material substrate can be any of a number of hydrophobic membranes, for example, polypropylene, polyethylene, polysulphone, PTFE or the like. Hydrophobic PVDF is preferred. The charge-modifying agent is preferably a polyamine epichlorohydrin resin and is present in the aqueous solution of the water-miscible organic solvent as between about 0.5% and 5% solids by weight, however, a solution of between about 1% and 3% solids by weight is preferred. The organic solvent can be any of the lower alcohols routinely used in industrial processing. Methanol, ethanol, isopropanol and mixtures thereof are preferred. This alcohol/water mixture is typically a 10–50% mixture by weight depending upon the solvent. The mixture is rendered mildly alkaline by the addition of a material such as NaOH. Preferably the solution is at a pH of between about 9.0 and 12.0.

Unlike other charge-modified, hydrophobic membranes known in the art, the charge-modified, hydrophobic membranes produced by the process of this invention are not subjected to a treatment with a secondary charge-modifying material such as tetraethylenepentamine. Historically, secondary charge-modifying agents have been suggested as a means to enhance the cationic charge of the primary charge-modifying agent as well as a means to crosslink the primary charge-modifying agent and enhance its bonding to the membrane surface.

The fixed formal positive charge groups as utilized in this invention are desirable in that they confer, to the substrate, excellent performance in binding macromolecules. When used in conjuction with hydrophobic membranes, the ion exchange capacity of the fixed formal positive charge groups and the hydrophobic nature of the membrane combine to provide excellent performance in applications in which it is desired to cause binding of macromolecules. Such applications include macromolecular blotting as well as filtration.

In their blotting applications, the cationically charged-modified hydrophobic membranes of this invention are used in the same manner that nitrocellulose, DBM-paper, DPT-paper and charge modified hydrophilic membranes have been used in the past. However, the combination of hydrophobic properties and the fixed formal positive charge provides the membranes of this invention with improved performance over the currently used blotting matrices. Furthermore, the materials of the present invention have been found to be effective when used under conditions in which blotting materials such as nylon have proven less than satisfactory, i.e., environments having high ionic strength.

Additionally, the materials of the present invention have a number of further advantages over traditional matrix materials such as nitrocellulose. For example, when used as a material for DNA blotting, nitrocellulose immobilizing matrices require high salt conditions in the buffer solution to perform adequately. The high salt conditions, however, lead to a high current flow requirement, i.e., up to about 5 amperes. These high current flows can generate heat which adversely affects the DNA being studied. Since high salt conditions are not required when using the materials of this invention, the current can be maintained in the milliampere range and thermal damage is therefore minimized or avoided entirely.

Overlaying of blots or transferred electrophoretograms can be carried out in the same manner with the materials of the present invention as they have been carried out in the past with other immobilizing matrix materials. Furthermore, because the binding ability of the materials of the instant invention is superior to that of the prior art materials, the instant materials exhibit enhanced ability to retain bound macromolecules during hybridization as well as the ability to maintain a strong signal throughout repeated recycling stages.

While the material of the invention has been found to be particularly useful in connection with the transfer of macromolecules from chromatographic gel substrates, it can be used in connection with substantially all other macromolecular blotting techniques, including specifically those techniques in which transfer occurs via convection or diffusion.

Charge-modified, hydrophobic membrane materials produced by the process previously described herein do not wet instantly when immersed into aqueous solutions. Rather, in applications in which the materials must be wet prior to use, such as in macromolecular blotting applications, it is necessary to prewet the materials with a water-miscible organic solvent either neat or in an aqueous solution. As before, the water miscible organic solvent can be any of the lower alcohols routinely used industrially (i.e., methanol, ethanol, isopropanol). These alcohols are preferably used in aqueous solutions with the ratio of alcohol to water varying from about 10–50% by weight depending upon the alcohol chosen.

As an alternative to an aqueous alcohol prewet step, membrane materials which will be used in applications requiring prewetting can be produced with an added surfactant or wetting agent incorporated into the matrix. In this case, the hydrophobic membrane is contacted with an aqueous solution of surfactant or wetting agent during the step of applying the charge-modifying coating or subsequent to the curing step. Suitable surfactant solutions include aqueous solutions of either ionic or non-ionic detergents such as Tween-20 (Trademark of ICI United States, Inc.) or Pluronic F-68 (Trademark of BASF Corp.). Suitable wetting agents include tetraglyme (tetraethylene glycol dimethyl ether), glycerin and the like. Such treatments render the material of the invention wettable as soon as it is contacted with aqueous media.

The invention will now be more specifically described in the following examples.

EXAMPLES

The examples described below illustrate the process of making and using cationically charge modified hydrophobic membranes. These membranes have utility for many applications including macromolecular blotting and filtration.

Broadly, the cationically charge modifying agents are coated onto a hydrophobic organic polymeric membrane by the following procedures: The hydrophobic membrane is first pre-wet in a water miscible organic solvent (i.e., alcohol) followed by exchange with water. This membrane is then coated by placing it in an aqueous solution of the charge modifying agent. Alternately, the process involves contacting the hydrophobic membrane substrate with an aqueous solution of a water miscible organic solvent (i.e., alcohol) which contains the charge modifying agent. The coating can be applied by dipping, slot coating, transfer rolling, spraying and the like. The coated membrane is then dried and cured under restraint. Suitable methods for drying and curing include the use of a heat transfer drum, hot air impingement, radiational heating or a combination of these methods.

EXAMPLE 1A

Preparation of Charge Modified Microporous Membrane

Sheets of microporous membranes (Immobilon P ™, a hydrophobic polyvinylidene fluoride, 0.45 micron pore size and Durapore ™, a hydrophilic polyvinylidene fluoride, 0.65 micron pore size, both available from Millipore Corporation, Bedford, Mass.) 15.0×25.0 cm were coated with a 3% (V/V) solution of Hercules R4308 adjusted to pH 10.56 with NaOH for 1 h at room temperature. In the case of the hydrophobic substrate the membrane was first pre-wet in methanol and exchanged with water before placing in the coating solution. The hydrophilic Durapore was placed directly into the coating solution. After coating, the membranes were air dried overnight and then placed between sheets of polyester film and heated under restraint at 121° C. for 3 min.

EXAMPLE 1B

Preparation of Charge Modified Microporous Membrane

Membrane samples similar to those of Example 1A were coated with a 3% solids by wt. solution of Hercules R4308 resin in 25% (V/V) isopropanol/water, adjusted to pH 10 using 50% (wt./wt.) NaOH. The membrane samples were immersed in this solution for 0.5 to 1.0 min. and then removed from the coating solution. Excess resin solution was removed by "squeegee" action using wiper bars. The membrane was then dried under restraint sandwiched between sheets of polyester film by contact with a heat transfer drum at a temperature of 95° C. for a period of 3 min. Samples of the membrane were characterized for thickness, initial methanol bubble point, flow time, BET surface area and ion exchange capacity (IEC). The results are summarized in Table 1.

TABLE 1

Chemical and Physical Characteristics of Charge Modified Hydrophobic PVDF Microporous Membrane

|  | Control | Charge Modified |
|---|---|---|
| Membrane |  |  |
| Thickness (mils) | 4.65 | 4.68 |
| Initial Bubble Point (psi)[1] | 11.2 | 11.36 |
| Flow time (cc/min/cm$^2$)[2] | 51.2 | 30.0 |
| BET Surface Area (m$^2$/g) | 6.47 | 5.5 |
| IEC Capacity[3] | 0 | 0.137 |

[1]47 mm diameter disks of the membrane samples were placed in a test holder which seals the edge of the disk. Above the membrane and in direct contact with its upper face, was a perforated stainless steel support screen which prevented the membrane from deforming or rupturing when air pressure was applied to it from below. Methanol was then placed above the membrane. Air pressure from a regulated supply was then applied beneath the membrane and increased until the first stream of air bubbles was emitted by the membrane. This pressure is termed the initial bubble point in psi.
[2]Flow time was measured in a similar device to that described above, following ASTM method #F317/72.
[3]To measure total IEC capacity, 47 mm disks of membrane samples were placed in 100 ml of 0.1 M HCl in 50% (V/V) methanol for 5 mins followed by air drying at room temperature for 1 h. The membrane disks were then wet in 100 mL of an 80% (V/V) methanol/water mixture, to which 2 ml of 5 M NaNO$_3$ solution was then added. The chloride ion concentration was then estimated by derivative titration with silver nitrate (0.0282 M Ag NO$_3$) using a Fisher computer aided titrimeter. The IEC capacity is then expressed as milliequivalents/g wt. of disk.

EXAMPLE 2

Binding of Nucleic Acid to Charge Modified Microporous Membranes

In this example, the binding of DNA to samples of microporous membranes coated with the charge modifying agent as described in Example 1A was investigated in a dot-blot manifold assay format. In this assay format, a sample of membrane forms the base of a well into which liquid can be placed for incubation with the membrane. The liquid can then be drawn through the membrane under vacuum. In this study a sample of double stranded DNA derived from the replicative form (RF) of the bacteriophage M13, which had been digested with the restriction enzyme Hind III (NE Biolabs) was used to compare DNA binding efficiencies of nylon to the charge modified PVDF surface. The RF-DNA was isolated as described by Messing, J., *Methods in Enzymology*, 101, Recombinant DNA [part C]:20–78, R. Wu, L. Grossman, K. Moldave, eds., Academic Press, New York (1983). The DNA was 3'end labelled using a commercial kit (NEN/Dupont, NEK 009) utilizing the enzyme terminal deoxynucleotidyl transferase and [alpha-$^{32}$P]3'-dATP as a label. Labeled DNA was combined with unlabeled material to give a specific activity of 10,000 cpm/ug DNA. The DNA was then added to the well of the dot-blot assay manifold in a volume of 0.050 mL in one of the following reagent systems: 0.125 M NaOH, 0.125×SSC (standard saline citrate, 18.75 mM NaCL, 2.1 mM Na Citrate), 10×SSC(1.5 M NaCl, 0.17 M Na Citrate, pH 7.4) and 25 mM Na Phosphate buffer (pH 7.4). In the latter two buffers, the DNA was rendered single stranded by heating to 100° C. for 5 minutes followed by rapid cooling in ice for 10 min. before application to the test membrane samples. After 30 min. any residual liquid was drawn through the membrane under vacuum. The membranes were then washed in the manifold under low vacuum with 0.100 mL of the same sample application buffer, and the membrane sheet was then removed and air dried. The individual membrane discs were then placed in scintillation counting fluid and the incorporation of $^{32}$P was measured.

Further samples were subjected to analysis for retention of radiolabelled DNA under conditions which simulated hybridization analysis as described in published literature (*Molecular Cloning*, pg. 387–389, T. Maniatis, E. F. Fritsch and J. Sambrook, eds., Cold Spring Harbor Press, 1982). In addition the bound DNA was also subjected to the alkali "stripping" conditions (0.4 M NaOH at 42° C. for 30 min.) used to remove bound radiolabeled DNA "probe". This simulated the conditions to which the membrane would be subjected if the blotted DNA was being reprobed. The results of a comparison of a hydrophobic and closely related hydrophilic substrate are summarized in Tables 2 and 3.

TABLE 2

Binding of DNA to Charge Modified Microporous Membranes Using a Dot-Blot Manifold Format Assay (Initial Retention of DNA)

| | % DNA retained of that applied[1] in the following buffers: | | |
|---|---|---|---|
| | Alkali[2] | 10 × SSC[3] | Phosphate[4] |
| Membrane Type: | | | |
| R4308 coated hydrophobic PVDF | 100 | 100 | 70.1 |
| R4308 coated hydrophilic PVDF | 95.2 | 0 | 64.7 |

TABLE 2-continued
Binding of DNA to Charge Modified Microporous
Membranes Using a Dot-Blot Manifold Format Assay
(Initial Retention of DNA)

| | % DNA retained of that applied[1] in the following buffers: | | |
|---|---|---|---|
| | Alkali[2] | 10 × SSC[3] | Phosphate[4] |
| Nylon[5] | 100 | 95.2 | 61.1 |

[1] 1 ug of M13 RF-DNA in one of the above sample buffer systems was applied in a volume of 0.050 mL at a specific activity of 9,000 to 13,000 cpm/ug DNA. After scintillation counting the ug DNA retained were calculated and expressed as % of 1 ug initial applied sample.
[2] 125 mM NaOH, 18,75 mM NaCl, 2.1 mM Na Citrate.
[3] 1.5 M NaCl, 0.17 M Na Citrate pH 7.4.
[4] 25 mm Na Phosphate, pH 7.4.
[5] Nylon sample used was Genescreen Plus (NEN/DuPont).

TABLE 3
Retention of Membrane Bound DNA After Exposure to the
Reagent Conditions of Hybridization Analysis and
and Alkali Recycling

| | | % DNA retained on the membrane surface[1] | |
|---|---|---|---|
| Sample Buffer | Membrane Type | Post-hybridization | Post-stripping |
| (1) Alkali | R4308 coated hydrophobic PVDF | 81.5 | 75.6 |
| | R4308 coated hydrophilic PVDF | 75.0 | 74.7 |
| | Nylon | 99.0 | 62.2 |
| (2) 10 × SSC | R4308 coated hydrophobic PVDF | 68.2 | 55.2 |
| | R4308 coated hydrophilic PVDF | 0 | 0 |
| | Nylon | 15.1 | 3.2 |
| (3) Phosphate | R4308 coated hydrophobic PVDF | 42.9 | 30.7 |
| | R4308 coated hydrophilic PVDF | 34.9 | 30.3 |
| | Nylon | 14.4 | 5.6 |

[1] Amount of DNA retained after exposure to the reagent conditions of hybridization analysis and one cycle of alkali stripping (to simulate removal of DNA probe during reprobing) is expressed as % of the initial DNA applied (1 ug) to the membrane.

The results of this study illustrate that charge modification of a microporous, hydrophobic PVDF membrane surface can produce a membrane exhibiting enhanced DNA binding and retention characteristics under conditions which simulate hybridization analysis and reprobing. The experimental conditions studied in this example provide a representative range of conditions as would likely be experienced by a membrane useful for solid phase nucleic acid blotting. Of special note is the complete absence of DNA binding to the R4308 coated hydrophilic PVDF surface under high ionic strength conditions (i.e. 10×SSC), which are used in the major application of Southern blotting. In contrast, the hydrophobic surface shows excellent binding of DNA. The observed performance advantage supports the theory that a hybrid ionic/hydrophobic microenvironment promotes more efficient macromolecular blotting. This is an important attribute of the charge modified hydrophobic surface.

EXAMPLE 3

Binding of Nucleic Acid to Charge Modified
Microporous Membranes and Simulation of Cycles of
Reprobing of the Blotted DNA In this example, membrane samples produced as described in Example 1A were used in a manifold dot-blot assay in a series of five cycles of hybridization analysis. The example illustrates the improved performance of the charge modified hydrophobic membrane over a currently available nylon substrate for this application.

In this assay, the M13-RF DNA isolated as described in Example 2 was radiolabeled as follows: (1) after digestion with the Hind III restriction enzyme a sample was 3'end labeled and was used to measure DNA binding as described in Example 2 using 10×SSC high ionic strength conditions; and (2) a sample of intact RF-DNA was nick-translated with (alpha-$^{32}$P) d-ATP using a commercial kit (NEN/DuPont, NEK 004) to achieve a specific activity of $10^7$ cpm/ug DNA and was used as a probe for hybridization analysis. This assay was then carried out as described in Example 2 using a dot-blot manifold (BioRad).

Two sets of samples of DNA digested with Hind III (1 ug in 0.050 mL) were absorbed to the test membranes as follows: (1) DNA that had been trace labeled with the $^{32}$P 3'end label. (This was used to determine the retention of DNA.) (2) DNA that was unlabeled. (This was used to follow the hybridization analysis with the nick-translated probe.) After one cycle of hybridization as described in Example 2, a set of samples were retained for scintillation counting while the rest were then alkali "stripped" to remove the radioactive probe DNA. These latter samples were then recycled through the hybridization process. This was repeated a total of five times. The results are summarized in Tables 4 and 5.

TABLE 4
DNA Binding/Rentention During Five Cycles of
Simulated Hybridization Analysis

| Membrane Type | Cycle # | ug DNA Retained[1] | % Total[2] |
|---|---|---|---|
| R4308 Coated Hydrophobic PVDF | 1 | 0.65 | 61.8 |
| | 2 | 0.26 | 22.8 |
| | 3 | 0.20 | 17.5 |
| | 4 | 0.21 | 18.4 |
| | 5 | 0.17 | 14.9 |
| Nylon[3] | 1 | 0.22 | 22.5 |
| | 2 | 0.018 | 1.8 |
| | 3 | 0.034 | 3.5 |
| | 4 | 0.027 | 2.7 |
| | 5 | 0.014 | 1.9 |

[1] M13 RF-DNA digested with Hind III was $^{32}$P 3' end labeled to a specific activity of 15,780 cpm/ug. Samples (1 ug in 0.05 ml) were bound to the above membrane samples in a dot-blot manifold as described in Example 2. The membranes were then removed from the manifold and subjected to cycles of hybridization analysis and "alkali stripping" conditions to simulate five cycles of reprobing. The amount of DNA retained was estimated by scintillation counting.
[2] Control values of DNA loaded onto the membrane samples before hybridization analysis are as follows:
R43098 coated hydrophobic PVDF 1.14 ug
nylon 0.98 ug
[3] Genescreen Plus nylon was used for comparison.

TABLE 5
Hybridization Analysis Using a Nick-Translated Probe:
A Simulation of Five Cycles of Reprobing

| Membrane Type | Cycle # | CPM Hybridized[1] |
|---|---|---|
| R4308 coated hydrophobic PVDF | 1 | 116,107 |
| | 2 | 113,362 |
| | 3 | 149,768 |
| | 4 | 221,768 |
| | 5 | 113,282 |
| Nylon[2] | 1 | 32,699 |
| | 2 | 40,713 |
| | 3 | 32,580 |
| | 4 | 69,189 |

TABLE 5-continued

Hybridization Analysis Using a Nick-Translated Probe:
A Simulation of Five Cycles of Reprobing

| Membrane Type | Cycle # | CPM Hybridized[1] |
|---|---|---|
| | 5 | 22,693 |

[1]Dot-blotted M13 RF-DNA was hybridized using "nick-translated" probe at a specific activity of 10 cpm/ug DNA following an established protocol (Molecular Cloning, pg. 387-389). After stringency washing, samples of membrane (in duplicate) with bound $^{32}$P probe were subjected to scintillation counting. The extent of hybridization was expressed as CPM bound to the adsorbed unlabeled Hind III digest of Lambda DNA.
[2]Genescreen Plus nylon used for comparison.

It is clear from the data presented in Table 4 that DNA is better retained on the R4308 coated hydrophobic PVDF surface compared to nylon. However, in both cases a large amount of the initial DNA adsorbed on these surfaces appears to be lost during the first cycle of use and then remains at a constant level. The hybridization analysis presented in Table 5 reflects the performance advantages of higher DNA retention by the charge modified hydrophobic PVDF surface. The improved dot-blot assay performance illustrates an important attribute of the hybrid ionic/hydrophobic membrane surface.

EXAMPLE 4

Dot-Blot Hybridization Analysis Using Charge Modified Microporous Membranes

In this example, samples of charge modified hydrophobic PVDF membrane, prepared by the process outlined in Example IB, were used in a dot-blot manifold assay to compare hybridization assay performance of the charge modified PVDF surface to nylon. Bacteriophage M13 RF-DNA digested with the restriction enzyme Hind III was heat denatured in 10×SSC and applied to charge modified hydrophobic PVDF and nylon membrane samples in 10×SSC in a dot-blot manifold as described in Example 2. A range of concentrations was applied as follows: 0.32, 1.6, 8.0, 40, 200 and 1000 ng/well. The dot-blotted DNA was then hybridized with a nicktranslated $^{32}$P labeled probe prepared as described in Example 3. An example of the resulting autoradiogram (Kodak XAR-5 film, 18 h exposure with intensifying screens) is shown in FIG. 1.

It is clear from the autoradiogram reproduced in FIG. 1 that the hybridization assay performance on the DNA dot-blotted to the charge modified hydrophobic PVDF is superior to that seen on nylon under the conditions of this experiment. Using the PVDF surface as little as 8 ng of blotted DNA can be detected on the autoradiograph. In contrast, DNA was only marginally detectable at the 200 ng level on the nylon membrane sample under the same conditions.

EXAMPLE 5

Southern Blotting Analysis Using Charge Modified Microporous Membranes

In the process of Southern blotting DNA fragments are separated by electrophoresis in an agarose gel and then transferred to a membrane support by capillary action. The following steps can be included in this process: (1) acid depurination to improved transfer of large DNA molecules, (2) alkali denaturation to render the DNA single stranded for transfer and (3) neutralization and equilibration with a high ionic strength transfer buffer (10×XSSC). For more details see Molecular Cloning, pg. 387-389.

After capillary transfer to the membrane, the blotted DNA is subjected to hybridization analysis. In the process of hybridization the following steps are carried out: (1) prehybridization is carried out first to reduce the non-specific binding of DNA to the membrane surface, (2) the membranes are exposed to homologous $^{32}$P labeled DNA probes (single stranded DNA which is complementary to the DNA bound to the membrane) under conditions which allow hybridization to occur between the probe and its target DNA sequences on the membrane, and (3) excess non-specifically retained probe is removed by washing under conditions of increasing stringency (for details see Molecular Cloning, pg. 387-389).

Figure 2:
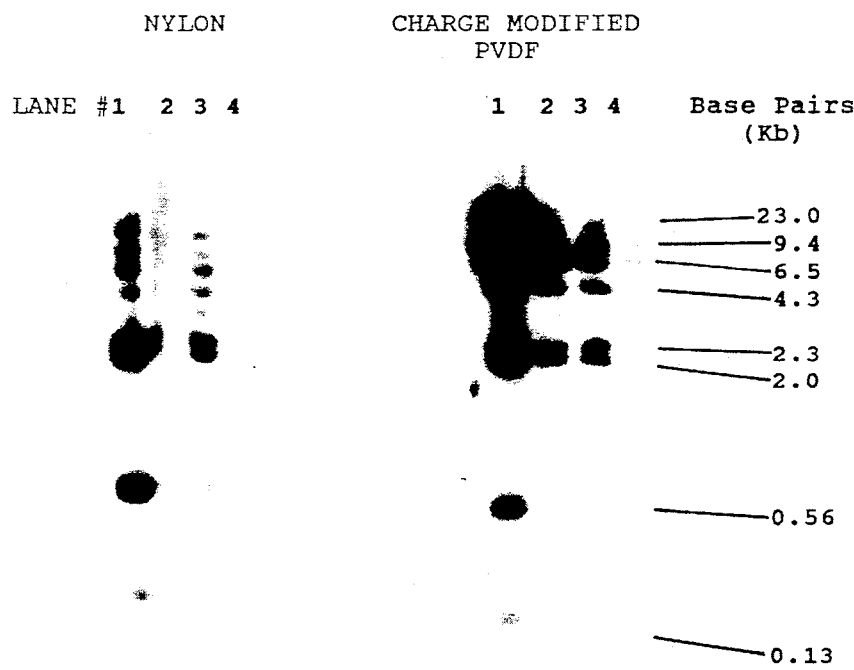
FIG. 2 is an autoradiogram comparing the materials of FIG. 1 in a Southern Blotting Analysis using a first $^{32}P$ labelled DNA probe.

In this example two experiments will be described:
(1) DNA fragments resulting from the Hind III digestion of Lambda DNA were labeled at the 5' ends with $^{32}$P dCTP (kit from DuPont/NEN). The resulting specific activity of the DNA probe was determined to be $10^6$ cpm/ug DNA, a total of 1 ug was used in this experiment. The retained DNA probe was visualized by exposure to X-ray film for 18 hours (FIG. 2). (2) In a similar experiment to that shown above, a DNA probe was labeled using many small random oligonucleotides as primers for DNA polymerase (Pharmacia Kit) to a specific activity of $10^9$ cpm/ug DNA and 0.2 ug was used for the experiment. The retained DNA probe was visualized by exposure to X-ray film for 10 min. (FIG. 3).

In FIG. 2, the DNA binding capacities of a nylon membrane and the charge modified hydrophobic surface are compared. It is clear from the data (with the exception of lane 2 for the nylon which is atypical) that the latter membrane gave better signal detection under the conditions of this experiment. In FIG. 3, essentially the same result is seen using a different probe having higher specific activity. The improved Southern blotting performance of the charge modified hydrophobic surface is an important attribute of this material as compared to nylon using accepted Southern blotting techniques.

Equivalents

Those skilled in the art will recognize or be able to ascertain, using no more than routine experimentation, many equivalents to the specific embodiments of the invention described herein. Such equivalents are intended to be covered by the following appended claims.

We claim:

1. A hydrophobic substrate comprising a hydrophobic, microporous membrane coated with a cross-linked, cationic charge-modifying polymer such that the ion-exchange capacity of the coated substrate is provided by fixed formal positive charge groups associated with the polymer, thereby providing a coated substrate having both ionic and hydrophobic surface effects.

2. A hydrophobic microporous membrane as in claim 1 which comprises polyvinylidene fluoride, polypropylene, polyethylene, polysulphone or polytetrafluoroethylene.

3. A membrane as in claim 1 wherein the fixed formal positive charge groups are provided by a water soluble, organic polymer having a molecular weight greater than about 1000, the polymer having a polymer chain having fixed formal positive charge groups as well as halohydrin groups.

4. A membrane as in claim 3 wherein the halohydrin groups comprise epichlorohydrin groups.

5. A membrane as in claim 3 wherein the fixed formal positive charge groups are selected from the group consisting of quaternary ammonium, quaternary phosphonium and quaternary sulfonium.

6. A membrane as in claim 3 wherein the fixed formal positive charge is provided by a polyamino epichlorohydrin surface coating.

7. A membrane as in claim 1 additionally comprising a surfactant or wetting agent incorporated into the material.

8. A method for producing a microporous membrane having both ionic and hydrophobic surface effects comprising:
   a. contacting a hydrophobic microporous membrane with a solution of (i) an organic polymer having a molecular weight of greater than about 100 daltons, wherein the polymer contains fixed formal positive charge groups and halohydrin groups; and (ii) an alkaline, aqueous organic solvent; and
   b. curing the coated microporous membrane.

9. A method as in claim 8 wherein the hydrophobic microporous membrane comprises a material selected from the group consisting of polyvinylidene fluoride, polypropylene, polyethylene, polysulphone and polytetrafluoroethylene.

10. A method as in claim 8 wherein the charge-modifying solution is maintained at a pH of between about 9.0 and about 12.0.

11. A method as in claim 8 wherein the curing comprises drying the coated hydrophobic substrate using heat.

12. A method as in claim 8 wherein the fixed formal positive charge groups are selected from the group consisting of quaternary ammonium, quaternary phosphonium and quaternary sulfonium.

13. A method as in claim 8 wherein the halohydrin groups comprise epichlorohydrin groups.

14. A method as in claim 8 comprising the additional step of contacting the coated hydrophobic substrate with an aqueous wetting agent or surfactant solution subsequent to the curing step.

15. A filtration material which comprises a hydrophobic, microporous membrane coated with a cross-linked, cationic polymer such that the ion exchange capacity of the coated membrane is provided by fixed, formal positive charge groups associated with the polymer, thereby providing a filtration material having both ionic and hydrophobic surface effects.

16. A method for producing a microporous membrane having both ionic and hydrophobic surface effects comprising:
   a. immersing a hydrophobic microporous membrane in an aqueous organic solvent containing a polyamine epichlorohydrin resin, for a time period sufficient to allow the resin to coat the membrane;
   b. removing the coated membrane from the aqueous organic solution; and
   c. curing the coated membrane.

17. The method according to claim 16 wherein the aqueous organic solution comprises alcohol in water.

18. The method according to claim 16 wherein the aqueous organic solution comprises about 25% isopropyl alcohol by volume in water and about 0.5% to 5.0% solids by weight of a polyamine epichlorohydrin resin.

* * * * *

UNITED STATES PATENT AND TRADEMARK OFFICE
CERTIFICATE OF CORRECTION

PATENT NO. : 5,004,543

DATED : April 2, 1991

INVENTOR(S) : Malcolm G. Pluskal, et al

It is certified that error appears in the above-identified patent and that said Letters Patent is hereby corrected as shown below:

Col. 13, line 16,
    Claim 8, line 6, delete "100" and insert ---1000---.

Signed and Sealed this

Sixteenth Day of February, 1993

Attest:

STEPHEN G. KUNIN

*Attesting Officer*    *Acting Commissioner of Patents and Trademarks*